United States Patent [19]

Thukamoto et al.

[11] 4,206,844
[45] Jun. 10, 1980

[54] PACKAGE FOR A STERILIZED MATERIAL

[75] Inventors: Sunao Thukamoto, Kawaguchi; Shyoji Yokokoji, Yashio, both of Japan

[73] Assignee: Toppan Printing Co., Ltd., Tokyo, Japan

[21] Appl. No.: 926,125

[22] Filed: Jul. 19, 1978

Related U.S. Application Data

[63] Continuation of Ser. No. 756,698, Jan. 4, 1977, abandoned.

[51] Int. Cl.² .................... B65D 85/00; B65D 65/38; A61L 3/00
[52] U.S. Cl. .................... 206/439; 206/459; 206/484.1; 428/35; 428/341; 428/342; 428/481; 428/483; 428/515; 428/516
[58] Field of Search .............. 428/35, 194, 481, 483, 428/515, 341, 342, 516; 206/438, 439, 459, 484, 484.1

[56] References Cited

U.S. PATENT DOCUMENTS

| | | | |
|---|---|---|---|
| 3,258,312 | 6/1966 | Olson | 206/439 |
| 3,903,335 | 9/1975 | Jones | 206/438 |
| 3,938,659 | 2/1976 | Wardell | 206/439 |
| 3,991,881 | 11/1976 | Augurt | 206/439 |

*Primary Examiner*—Paul J. Thibodeau

[57] ABSTRACT

A package of, for example, a medical instrument adapted to be sterilized by ethylene oxide gas, which comprises a package body in which a paper substrate is coated with a polyester resin emulsion layer, and a thermoplastic resin emulsion layer, and a thermoplastic resin emulsion layer is laminated on said polyester resin emulsion layer, and a covering sheet heat-sealed to the thermoplastic resin emulsion layer around a packed material, thereby hermetically sealing the package, said package having an indicator enabling the completion of disinfection to be visibly recognized.

9 Claims, 5 Drawing Figures

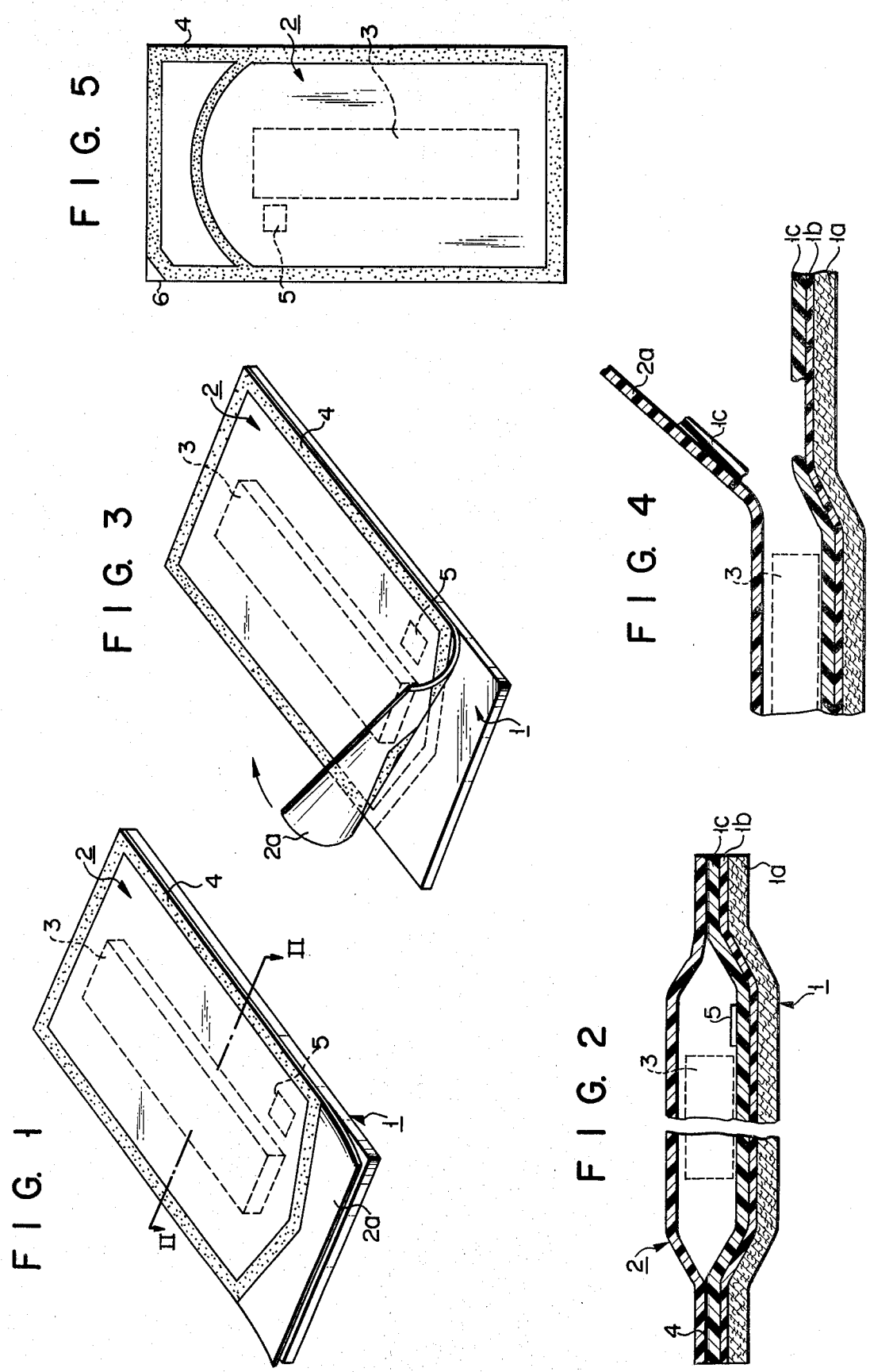

PACKAGE FOR A STERILIZED MATERIAL

This is a continuation of application Ser. No. 756,698, filed Jan. 4, 1977 and now abandoned.

BACKGROUND OF THE INVENTION

This invention relates to a package of a material being disinfected which prevents filaments or dust of paper material from being scattered from the package when it is opened.

A prior art package of a material being disinfected, for example, a medical instrument is so constructed as to be peeled open, and is accompanied with the undesirable possibility of, for example, filaments or dust of paper material being scattered from the package when it is opened and being deposited on a medical instrument received in the package. Further, a package in which paper is not used as a substrate is prepared from plastic film alone. Such package is sealed by closing its opening with porous material such as absorbent cotton or by tightly twisting said opening, thus failing properly to function as a package.

Further, a plastic film package coated with an organic solvent type lacquer is used with the medical instruments whose material is often prepared from soft vinyl chloride. This type of plastic film package has the drawbacks that a large content of plasticizer in the package gives rise to blocking between the package and received material and the residual solvent contained in the package tends to affect the received material.

SUMMARY OF THE INVENTION

It is accordingly an object of this invention to provide a package which is saved from the drawbacks accompanying the prior art package; enables a packed material such as a medical instrument to be disinfected by gas while being received in said package; and prevents filaments of, for example, paper material used as a substrate from being scattered out of the package when it is opened.

Another object of the invention is to provide a package which does not harmfully affect a material received therein, nor gives rise to blocking between the package and the received material, if it is prepared from non-rigid vinyl chloride.

To attain the above-mentioned objects, this invention provides a package of a sterized material comprising a package body in which one side of a germ-proof paper substrate having sufficient breathability is coated with a thermoplastic polyester resin emulsion layer, and a different kind of thermoplastic resin emulsion layer is laminated on said polyester resin emulsion layer; and a covering sheet heat-sealed to the thermoplastic resin emulsion layer around the packed material.

BRIEF DESCRIPTION OF THE DRAWING

FIG. 1 is an oblique view of a package according to one embodiment of this invention;

FIG. 2 is a cross sectional view on line II—II of FIG. 1;

FIGS. 3 and 4 are oblique and cross sectional views showing the manner in which the package of FIG. 1 is opened; and FIG. 5 is a plan view of a package according to another embodiment of the invention.

DESCRIPTION OF THE PREFERRED EMBODIMENTS

There will now be described a package embodying this invention by reference to the accompanying drawings. The package shown in FIG. 1 embodying this invention comprises a package body 1; and a covering sheet 2 stretched over the upper surface of said body 1, a packed material 3 is received between said package body 1 and covering sheet 2. The package body 1 and covering sheet 2 are attached to each other in airtightness by means of a bonding material 4 heat-sealed at a prescribed width around the object of disinfection 3. One end of the covering sheet 2 is not bonded, but is left free to provide a grip strip 2a. Referential numeral 5 denotes an indicator for showing the completion of disinfection or sterilization.

As illustrated in FIG. 2, the package body 1 is a laminate formed by coating a polyester resin emulsion layer 1b on one side of a paper substrate 1a and mounting a thermoplastic resin emulsion layer 1c on said plyester resin emulsion layer 1b. The paper substrate 1a is made of breathable, germ-proof material, for example, high quality paper, kraft paper or these forms of paper impregnated with a proper amount of resin, for example, rubber latex.

The polyester resin emulsion layer 1b may suitably consist of a known emulsion of thermoplastic polyester resin such as isophthalic acid, diethylene glycol or sodium 5-sulfonate, selection of a polyester resin emulsion for use with the package of this invention is for the following important reason. It is undesirable to replace the polyester resin emulsion by natural resins such as gelatin, casein, polyamino acid, starch, dextrin, gum arabic, sodium alginate and carboxymethyl cellulose. This is because such natural resins provide suitable beds in which microbes and moulds are grown and become unsanitary and moreover are less adapted to be coated on the paper substrate of a package.

Further, substitution of the polyester resin emulsion by that of other forms of resin such as acrylic resin, polyvinyl pyrrolidone, a copolymer of polyvinyl pyrrolidone and vinyl acetate, or polyvinyl alcohol causes part of the paper substrate of the package to be torn off, when the package is peeled open, failing to attain the object of this invention. Silicone resin has too unsatisfactory adhesivity to any other form of resin for use with the package.

The thermoplastic resin emulsion layer 1c is formed of an emulsion of thermally fusible thermoplastic resin such as polyolefins, denatured polyolefins, ionomer resin or, ethylene-vinyl acetate copolymer. Particularly preferred are polyolefins and denatured polyolefins.

The polyester resin emulsion layer 1b and thermoplastic resin 1c should preferably be applied in an amount of 1 to 10 g/m$^2$ (dry basis) in consideration of the required breathability of the entire laminated mass of the package body 1. The laminated mass of the package body 1 is desired to have an air permeability of 50 to 500 second/100 cc air is measured by the Gurley air permeability. Therefore, it is advised to control application of the above-mentioned emulsions 1b, 1c in consideration of the material of the paper substrate 1a and the concentration of said emulsions.

The covering sheet 2 may suitably be formed of material thermally fusible with the thermoplastic resin emulsion layer 1c. Namely, the covering sheet 2 may be formed of thermoplastic resin film, or film coated or impregnated with said thermoplastic resin. Particularly where a gas disfection indicator 5 is provided in the subject package, it is preferred to prepare the covering sheet 2 from a transparent film, for example, polyethylene film, polypropylene film, polyethylene-polyamide film, polyethylene-polyester laminated film or polypropylene-polyester laminated film, polyethylenecellophane laminated film, polyethylene-stretched polypropylene laminated film.

According to this invention, an object of disinfection 3 is placed on the package body 1. The covering sheet 2 is stretched over the object of disinfection 3. The peripheral portions of the package body 1 and covering sheet 2 are heat-sealed. The heat-sealed portion 4 is chosen to have such a bonded strength as can be easily peeled off by the hand. Namely, a bonded strength of, for example, 75 to 500 g/15 mm (a value indicated by a heat sealed portion 4 15 mm wide when pulled through an angle of 180°) is desired in consideration of the mechanical strength of the package and its readiness for peeling.

With the package of this invention, the polyester resin emulsion layer 1b coated on the paper substrate 1a has a great bonding strength thereto. When dried, said polyester resin emulsion layer 1b has a higher degree of crystallization than the thermoplastic resin. Accordingly, a bonded strength between the polyester resin emulsion layer 1b and thermoplastic resin emulsion layer 1c is relatively smaller than that of the polyester resin emulsion layer 1b bonded to the paper substrate 1a. Therefore, where the package is opened after completion of gas disinfection, by peeling off the covering sheet 2 in the direction of an arrow indicated in FIG. 3 with the grip strip 2a grasped by the hand, then peeling easily takes place between the polyester resin emulsion layer 1b and the thermoplastic resin emulsion layer 1c. In this case, only that part of the heat-sealed portion 4 which is constituted by the thermoplastic resin layer 1c is broken, and the package is opened with said broken portion of the thermoplastic resin emulsion layer 1c attached to the covering sheet 2. Therefore, the paper substrate 1a is not affected by peeling in any way, fully preventing dust of paper material or paper fibers from being scattered from the package body 1.

The package of this invention whose substrate is formed of paper has good breathability, making it possible to disinfect a packed material by gas, for example, ethylene oxide, while said material is received in the package. Further, when the subject package encloses an article made of nonrigid vinyl-chloride containing a large amount of placticizer, thermal fusion does not arise between the package and the disinfected material, thus offering convenience from the standpoint of sanitation. The subject package further has practically prominent advantage that since the emulsion layers 1b, 1c are coated on the paper substrate 1a with water used as a solvent, no harmful effect is exerted by any residual water solvent on human beings as well as on a disinfected material received in the package.

A package of FIG. 5 according to another embodiment of this invention is different from that of FIG. 1 in that in the embodiment of FIG. 5 that side of the heat-sealed portion 4 on which peeling is commenced has an arciform to admit of easy peeling, whereas, in the embodiment of FIG. 1, the peel-starting side of the heat-sealed portion 4 has an angular convex form, and that in the embodiment of FIG. 5, substantially all the periphery of the package is heat-sealed with a triangular grip strip 6 provided in one corner. The embodiment of FIG. 5 has the advantage that since only a small grip strip 6 is left on the package there is less possibility than in the embodiment of FIG. 1 that dust or dirt is gathered in a space lying between the grip strip 6 and package or said intervening space is contaminated by any other foreign matter.

There will not be described an indicator 5 used with a package embodying this invention. The indicator 5 is directly printed on the inside of the package itself or on a separate sheet of paper which is placed in the package together with a medical instrument. Therefore, the following description is concentrated on the chemical composition of printing ink used as an indicator.

An indicator ink composition for use with ethylene oxide gas is impressed, for example, on the inside of a package of a medical instrument. This indicator enables the completion of disinfection of a medical instrument received in the package to be visibly displayed by an irreversible color change caused by reaction between the indicator and ethylene oxide gas.

The indicator ink composition of this invention is obviously not only provided with such fluidity and adhesivity as are demanded of an ordinary form of ink, but also contains calcium halide capable of producing alkaline calcium hydroxide by reaction with ethylene oxide as expressed by the following chemical formula (where X denotes a halogen element).

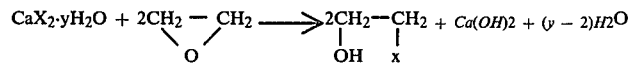

and two or more pH-indicators which change color in the pH region of 2 to 10.

Where the indicator ink composition of this invention has to hold acidity before reaction with ethylene oxide, then the ink composition is mixed with an organic acid such as citric acid. Where the ink composition must preserve weak alkalinity, it is advised to add, for example, hexamethylene tetramine to said ink composition. Where the indicator prevents color change in an acid region having a smaller pH level than 7, then the latter additive (hexamethylene tetramine) is mixed with the ink indicator, if the indicator shows color change in a neutral or weak alkaline pH region. In any case, the color-presenting reaction of the indicator with ethylene oxide gas which results from the growth of an alkaline material as seen from the above chemical formula detects completion of disintection. Therefore, application of metal halide, for example, calcium bromide ($CaBr_2.2H_2O$) offers convenience, because reaction of said metal halide with ethylene oxide produces calcium hydroxide ($Ca(OH)_2$) having relatively high alkalinity. Further, the ink composition of this invention which includes two or more pH indicators enables color change to proceed stepwise, and consequently the progress of disinfection to be distinctly recognized by the condition of color change.

There will now be described a combination of pH indicator. For instance, bromocresol green (BCG) combined with methyl yellow (MY) presents a bright red color in an acid region and a bluish green color in an alkaline region. Bromothymol blue (BTB) combined with methyl red (MR) displays color shift from red to bluish green with a neutral region substantially taken as a border. The ink composition of this invention which contains at least two pH indicators displays a color shift from red to bluish green according as reaction proceeds between said composition and ethylene oxide. In this case, a color produced remains unchanged for a sufficient length of time and moreover shows an increased shade.

Some ink compositions including indicators are given below.

| Ink composition 1: | |
| --- | --- |
| Ingredients | Parts by weight |
| Ethyl cellulose | 120 |
| Calcium bromide (CaBr$_2$. 2H$_2$O) | 30 |
| Citric acid | 10 |
| Bromocresol green | 2 |
| Methyl yellow | 1 |
| Ethyl acetate | 150 |
| Isopropyl alcohol | 150 |
| Ink composition 2 | |
| Ingredients | Parts by weight |
| Ethyl cellulose | 12 |
| Calcium bromide (CaBr$_2$. 2H$_2$O) | 7 |
| Bromothymol blue | 1 |
| Methyl red | 0.5 |
| Aexamethylene tetramine | 4 |
| Ethyl acetate | 30 |
| Isopropyl alcohol | 40 |

There will now be described an example of manufacturing a package embodying this invention.

EXAMPLE 1

A sheet of paper impregnated with styrene-butadiene latex was used as a substrate 1 of the subject package. The following emulsion layers were applied to the package.

| Polyester emulsion layer | |
| --- | --- |
| Linear polyester emulsion (WD size, manufactured by Eastman Kodak Co.) | 10 parts by weight |
| Water | 5 parts by weight |
| Amount of emulsion layer applied | 5 g/m$^2$ |
| Adhesive emulsion layer | |
| Polyethylene-base emulsion (manufactured by Zaikthene A Seitetsu Kagaku Co., Ltd.) | 5 parts by weight |
| Water | 10 parts by weight |
| Amount of adhesive emulsion layer applied | 7 g/m$^2$ |

The above-mentioned emulsion layers were heat-sealed to a covering sheet formed of low density polyethylene to provide a package body. When the package body was peeled open, easy peeling was effected between the polyester resin emulsion layer and thermoplastic resin emulsion layer constituting the heat-sealed portion without the scattering of dusts of, for example, substrate paper material out of the package body.

Where the thermoplastic resin emulsion layer was formed of, for example, an emulsion of polypropylene, denatured polyolefins such as ethylene-vinyl chloride copolymer, ethylene-acrylic acid copolymer, ionomer resin or ethylenevinyl acetate copolymer, the package body was easily peeled open without the scattering of dusts of, for example, substrate paper material.

What we claim is:

1. A package of a sterilized material comprising a package body in which one side of a breathable, germ-proof paper substrate is coated with a water based thermoplastic polyester resin emulsion layer, and an emulsion layer of a water based thermoplastic resin selected from the group consisting of polyolefins, denatured polyolefin and ionomer resin, which is laminated on said polyester resin emulsion layer; and a covering sheet heat-sealed to the thermoplastic resin emulsion layer surrounding a disinfected object contained in the package body; the inside of said package being provided with means for indicating the completion of sterilization, said means comprising an ink composition containing a calcium halide for producing alkaline calcium hydroxide upon reaction and sterilization of the package with ethylene oxide and at least two pH-indicators which change color in the pH-region of 2 to 10, each pH-indicator having a different color-change region from each other to produce a stepwise color change as sterilization progresses.

2. The package according to claim 1, wherein the covering sheet is one selected from the group consisting of polyethylene film, polypropylene film, polyethylene-polyamide laminated film, polyethylenepolyester laminated film, polypropylenepolyester laminated film, ployethylene-cellophane laminated film and polyethylene-stretched polypropylene laminated film.

3. The package according to claim 1, wherein the whole laminated mass has an air permeability of 50 to 500 second/100 cc air as measured by the Gurley air permeability.

4. The package according to claim 1, wherein a bonded strength between the laminated mass and covering sheet ranges between 75 and 500 g/15 mm.

5. The package according to claim 1, wherein the polyester resin emulsion and thermoplastic resin emulsion are applied in an amount ranging from 1 to 10 gm/$^2$.

6. The package according to claim 1, wherein the breathable, germ-proof paper substrate is formed of one selected from the group consisting of high quality paper, kraft paper, and resin-impregnated paper.

7. A package according to claim 1, wherein the pH-indicators consist of bromocresol green and methyl yellow.

8. The package according to claim 1, wherein the pH-indicators consist of bromothymolblue and methyl red.

9. A package according to claim 1, wherein the calcium halide is calcium bromide.

* * * * *